(12) United States Patent
Ohara et al.

(10) Patent No.: US 7,041,700 B2
(45) Date of Patent: May 9, 2006

(54) SUBSTITUTED BENZOPYRAN DERIVATIVES AGAINST ARRHYTHMIA

(75) Inventors: Yoshio Ohara, Funabashi (JP); Kazuhiko Ohrai, Funabashi (JP); Kazufumi Yanagihara, Funabashi (JP); Yukihiro Shigeta, Funabashi (JP); Toru Tsukagoshi, Funabashi (JP); Toru Yamashita, Minamisaitama-gun (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 10/479,118

(22) PCT Filed: Jun. 17, 2002

(86) PCT No.: PCT/JP02/06012

§ 371 (c)(1),
(2), (4) Date: Nov. 28, 2003

(87) PCT Pub. No.: WO03/000675

PCT Pub. Date: Jan. 3, 2003

(65) Prior Publication Data

US 2004/0152763 A1 Aug. 5, 2004

(30) Foreign Application Priority Data

Jun. 25, 2001 (JP) .............................. 2001-190594

(51) Int. Cl.
*A61K 31/35* (2006.01)

(52) U.S. Cl. ....................... 514/456; 549/466; 549/467

(58) Field of Classification Search ................ 549/466, 549/467; 514/456
See application file for complete search history.

(56) References Cited

U.S. PATENT DOCUMENTS

| 5,095,016 A | * | 3/1992 | Ohtuka et al. ............ 514/233.5 |
| 5,097,037 A | | 3/1992 | Matsumoto et al. |
| 5,276,168 A | | 1/1994 | Atwal |
| 5,420,314 A | | 5/1995 | Katsuki et al. |
| 5,466,817 A | | 11/1995 | Atwal |
| 5,624,954 A | * | 4/1997 | Evans et al. ................ 514/456 |
| 5,679,706 A | | 10/1997 | D'Alonzo et al. |
| 6,150,356 A | | 11/2000 | Lloyd et al. |

FOREIGN PATENT DOCUMENTS

| EP | 0 409 165 A2 | 1/1991 |
| EP | 0 462 761 A2 | 12/1991 |
| EP | 0 535 377 A2 | 4/1993 |
| JP | A-52-91866 | 8/1977 |
| JP | A-56-57785 | 5/1981 |
| JP | A-56-57786 | 5/1981 |
| JP | A-58-67683 | 4/1983 |
| JP | A-58-188880 | 11/1983 |
| JP | A-62-273972 | 11/1987 |
| JP | A-2-141 | 1/1990 |
| JP | A-3-141286 | 6/1991 |
| JP | A-5-301878 | 11/1993 |
| JP | A-5-507645 | 11/1993 |
| JP | A-7-285983 | 10/1995 |
| JP | A-10-87650 | 4/1998 |
| JP | A-11-209366 | 8/1999 |
| JP | A-2001-151767 | 6/2001 |
| WO | WO 95/34547 | 12/1995 |
| WO | WO 00/12077 A1 | 3/2000 |

OTHER PUBLICATIONS

Lloyd, J. et al Preparation of benzopyran, tetrahydroquinoline, pyro[2,3-b]pyridine, and indane derivatives as potassium channel inhibitors (2000) CA 132:207763.*

Hiessboeck, R et al 'Synthesis and in vitro multidrug resistance modulating activity of a series of dihydrobenzopyrans and tetrahydroquinolines' (1999) CA 131:87799.*

(Continued)

*Primary Examiner*—Amelia A. Owens
(74) *Attorney, Agent, or Firm*—Oliff & Berridge, PLC

(57) ABSTRACT

This invention relates to benzopyran derivatives of the formula (1) or the formula (2) wherein $R^1$ and $R^2$ represent independently of each other hydrogen atom or $C_{1-6}$ alkyl group, $R^3$ represents hydroxyl group or $C_{1-6}$ alkylcarbonyloxy group, $R^4$ represents hydrogen atom or $C_{1-6}$ alkyl group, $R^5$ represents $C_{1-6}$ alkyl group substituted with $C_{6-14}$ aryl group or heteroaryl group, $R^6$ represents $C_{1-6}$ alkyl group, $C_{1-6}$ alkoxy group, halogen atom, nitro group, $C(O)NH_2$, $C(O)NHR^8$ or $C(O)NR^8R^9$, or pharmaceutically acceptable salts thereof. These compounds are useful as an antiarrhythmic agent

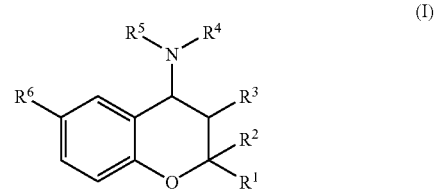

(I)

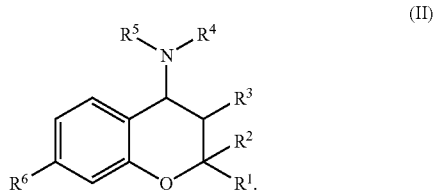

(II)

11 Claims, No Drawings

OTHER PUBLICATIONS

Rovnyak, GC et al 'Preparation of 4-(arylamino)benzopyrans and analogs as cardiovascular agents' (1998) CA 130: 13916.*

Ding CZ et al 'Syntheis of 4-(N-alkyl-N-heteroarylamino)-3,4-dihydro-3-hydroxy-2,2-dimethyl-2H-1-benzopyran-6-carbonitrile derivatives via an unusual 1,4-oxygen to nitrogen heteroaryl migration' (1996) CA 125:195558.*

Vong AKK et al Preparationof 4-benzoylamino-3,4-dihydro-2H-benzopyran-3-ol derivatives and analogs as therapeutic agent (1996) CA 124:260843.*

Blackburn, TP et al 'Stereochemical differentiation of anticonvulsant and antihyperstnnsive effects in 4-(fluorobenzoylamino)benzopyrans' (1995) CA 124:86760.*

Evans, JM et al 'Electron impact behavior of trans-4-benzolyamino-2H-1-benzopyran-3-ols: evidence for an oxygen migration with loss of a benzopyrane' (1995) 123: 198143.*

Conners et al., "The Synthesis and Potassium Channel Blocking Activity of Some (4-Methanesulfonamidophenoxy)propanolamines as POtential Class III Antiarrhythmic Agents," *J. Med. Chem*, vol. 34, No. 5, pp. 1570-1577, 1991.

Nicolau et al., "Natural Product-like Combinatorial Libraries based on Privileged Structures 3. The 'Libraries from Libraries' Principle for Diversity Enhancement of Benzopyran Libraries," *J. Am. Chem. Soc.*, vol. 122, No. 41, pp. 9968-9976, 2000.

Evans et al., "Synthesis and Antihypertensive Activity of 6,7-Disubstituted trans-4-Amino-3,4-digydro-2,2-dimethyl-2H-1-benzopyran-3-ols," *J. Med. Chem.*, vol. 27, No. 9, pp. 1127-1131, 1984.

Ashwood et al., "Synthesis and Antihypertensive Activity of 4-(Cyclic amido)-2H-1-benzopyrans," *J. Med. Chem.*, vol. 29, No. 11, pp. 2194-2201, 1986.

North et al., Synthesis of 6-Cyano-2,2-dimethyl-2H-1-benzopyran and other Substituted 2,2-dimethyl-2H-1-benzopyran, *J. Org. Chem.*, vol. 60, No. 11, pp. 3397-3400, 1995.

Bell et al., "Copper(I) Iodide: A catalyst for the Improved Synthesis of Aryl Propargyl Ethers," *Synthesis*, pp. 707-712, 1995.

* cited by examiner

SUBSTITUTED BENZOPYRAN DERIVATIVES AGAINST ARRHYTHMIA

TECHNICAL FIELD

The present invention relates to substituted benzopyran derivatives having the prolongation effect on the refractory period used for the treatment of arrhythmia in mammals including human being.

BACKGROUND ART

As benzopyran derivatives, 4-acylaminobenzopyran derivatives exemplified by Cromakalim (Jananese Patent Application Laid-open No. Sho 58-67683) have been known. These 4-acylaminobenzopyran derivatives exemplified by Cromakalim are known to open ATP sensitive $K^+$ channel so as to be effective for the treatment of hypertension and asthma, but there has not been any mention as to the treatment of arrhythmia based on the prolongation effect on the refractory period.

At present, conventional anti-arrhythmic agents having the prolongation effect on the refractory period as a main mechanism (such as Class I drugs of antiarrhythmic agent classification according to Vaughan Williams, or d-sotalol belonging to Class III) have been the therapeutic problems in inducing highly dangerous arrhythmia leading to the sudden death from such as torsades de pointes among others due to prolongation of action potential in ventricular muscle correlated to the prolongation effect on the refractory period. Thus, treating agents with less adverse effect have been highly desired.

DISCLOSURE OF INVENTION

The inventors of the present invention have investigated compounds having the prolongation effect on the refractory period selective for atrium muscle rather than for ventricular muscle, and found that the compound of the formula (1) or the formula (2) has the prolongation effect on the refractory period selective for atrium muscle without any influence on the refractory period and action potential in ventricular muscle.

The inventors of the present invention have eagerly investigated benzopyran derivatives, and found that the compound of the formula (1) or the formula (2) has the strong prolongation effect on the refractory period to be useful as an antiarrhythmic agent to their delight. Thus, the present invention has been accomplished.

The present invention relates to a benzopyran derivative of the formula (1) or the formula (2)

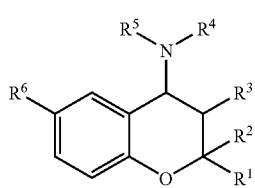

(1)

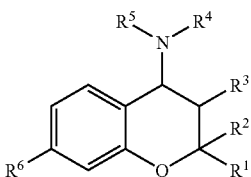

(2)

wherein $R^1$ and $R^2$ represent independently of each other hydrogen atom or $C_{1-6}$ alkyl group (wherein said alkyl group may be optionally substituted with halogen atom, $C_{1-6}$ alkoxy group or hydroxyl group);

$R^3$ represents hydroxyl group or $C_{1-6}$ alkylcarbonyloxy group;

$R^4$ represents hydrogen atom or $C_{1-6}$ alkyl group;

$R^5$ represents $C_{1-6}$ alkyl group substituted with $C_{6-14}$ aryl group or heteroaryl group [wherein said $C_{1-6}$ alkyl group may be optionally substituted with hydroxyl group, methyl group, and said $C_{6-14}$ aryl group or heteroaryl group may be optionally substituted with 1 to 3 $R^7$ (wherein $R^7$ may be optionally substituted with halogen atom, nitro group, cyano group, hydroyxl group, formyl group, formamide group, amino group, $C_{1-6}$ alkyl group, $C_{1-6}$ alkoxy group (wherein said $C_{1-6}$ alkyl group, $C_{1-6}$ alkoxy group may be optionally substituted with halogen atom), $C_{3-6}$ cycloalkyl group, $C_{1-6}$ alkylamino group, di-$C_{1-6}$ alkylamino group, $C_{1-6}$ alkylcarbonylamino group, $C_{1-6}$ alkylsulfonylamino group, aminocarbonyl group, $C_{1-6}$ alkylaminocarbonyl group, di-$C_{1-6}$ alkylaminocarbonyl group, $C_{1-6}$ alkylcarbonyl group, $C_{1-6}$ alkoxycarbonyl group, aminosulfonyl group, $C_{1-6}$ alkylsulfonyl group, carboxyl group or benzoyl group (wherein said benzoyl group may be optionally substituted with $C_{1-6}$ alkyl group, $C_{1-6}$ alkoxy group, halogen atom, nitro group or cyano group))] or straight-chain $C_{5-8}$ alkyl group (wherein said $C_{5-8}$ alkyl group may be optionally substituted with fluorine atom or hydroxyl group);

$R^6$ represents $C_{1-6}$ alkyl group (wherein said alkyl group may be optionally substituted with hydroxyl group, carboxyl group, amino group, $C_{1-6}$ alkylamino group, di-$C_{1-6}$ alkylamino group, $C(O)OR^8$, $NHSO_2R^8$, $C(O)NH_2$, $C(O)NHR^8$ or $C(O)NR^8R^9$ (wherein $R^8$ and $R^9$ represent independently of each other $C_{1-6}$ alkyl group substituted with $C_{6-14}$ aryl group or heteroaryl group or $C_{1-6}$ alkyl group)), $C_{1-6}$ alkoxy group, halogen atom, nitro group, $C(O)NH_2$, $C(O)NHR^8$ or $C(O)NR^8R^9$ (wherein $R^8$ and $R^9$ represent independently of each other $C_{1-6}$ alkyl group substituted with $C_{6-14}$ aryl group or heteroaryl group or $C_{1-6}$ alkyl group);

or a pharmaceutically acceptable salt thereof.

The compound according to the present invention has the strong prolongation effect on the refractory period and it can be used as a drug for treating arrhythmia.

Respective substituents for the compound (1) according to the present invention are concretely defined below.

Furthermore, "n" means normal, "i" means iso, "s" means secondary, "t" means tertiary, "c" means cyclo, "o" means ortho, "m" means meta and "p" means para in this specification.

Examples of $C_{1-6}$ alkyl group are such as methyl, ethyl, n-propyl, i-propyl, n-butyl, i-butyl, s-butyl, t-butyl, 1-pentyl, 2-pentyl, 3-pentyl, i-pentyl, neopentyl, 2,2-dimethylpropyl, 1-hexyl, 2-hexyl, 3-hexyl, 1-methyl-n-pentyl, 1,1,2-trimethyl-n-propyl, 1,2,2-trimethyl-n-propyl, 3,3-dimethyl-n- butyl, trifluoromethyl, trifluoroethyl, pentafluoroethyl, cyanomethyl, hydroxymethyl and the like.

Preferably, methyl, ethyl, n-propyl, i-propyl and n-butyl may be mentioned.

Examples of halogen atom are such as fluorine atom, chlorine atom, bromine atom and iodine atom. Preferably, fluorine atom, chlorine atom and bromine atom may be mentioned.

Examples of $C_{1-6}$ alkoxy group are such as methoxy, trifluoromethoxy, ethoxy, n-propoxy, i-propoxy, n-butoxy, i-butoxy, s-butoxy, t-butoxy, 1-pentyloxy, 2-pentyloxy, 3-pentyloxy, i-pentyloxy, neopentyloxy, 2,2-dimethylpropoxy, 1-hexyloxy, 2-hexyloxy, 3-hexyloxy, 1-methyl-n-pentyloxy, 1,1,2-trimethyl-n-propoxy, 1,2,2-trimethyl-n-propoxy, 3,3-dimethyl-n-butoxy and the like.

Preferably, methoxy, ethoxy, n-propoxy and i-propoxy may be mentioned.

Examples of $C_{1-6}$ alkylcarbonyloxy group are such as methylcarbonyloxy, ethylcarbonyloxy, n-propylcarbonyloxy, i-propylcarbonyloxy, n-butylcarbonyloxy, i-butylcarbonyloxy, s-butylcarbonyloxy, t-butylcarbonyloxy, 1-pentylcarbonyloxy, 2-pentylcarbonyloxy, 3-pentylcarbonyloxy, i-pentylcarbonyloxy, neopentylcarbonyloxy, t-pentylcarbonyloxy, 1-hexylcarbonyloxy, 2-hexylcarbonyloxy, 3-hexylcarbonyloxy, 1-methyl-n-pentylcarbonyloxy, 1,1,2-trimethyl-n-propylcarbonyloxy, 1,2,2-trimethyl-n-propylcarbonyloxy, 3,3-dimethyl-n-butylcarbonyloxy and the like.

Preferably, methylcarbonyloxy, ethylcarbonyloxy, n-propylcarbonyloxy, i-propylcarbonyloxy, n-butylcarbonyloxy and t-butylcarbonyloxy may be mentioned.

Examples of $C_{6-14}$ aryl group are such as phenyl, biphenylyl, naphthyl, anthryl, phenanthryl and the like.

Preferably, phenyl may be mentioned.

Examples of heteroaryl group are such as 2-thienyl group, 3-thienyl group, 2-furyl group, 3-furyl group, 2-pyranyl group, 3-pyranyl group, 4-pyranyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 4-isobenzofuranyl group, 5-isobenzofuranyl group, 2-benzothienyl group, 3-benzothienyl group, 4-benzothienyl group, 5-benzothienyl group, 6-benzothienyl group, 7-benzothienyl group, 1-isobenzothienyl group, 4-isobenzothienyl group, 5-isobenzothienyl group, 2-chromenyl group, 3-chromrenyl group, 4-chromenyl group, 5-chromenyl group, 6-chromenyl group, 7-chromenyl group, 8-chromenyl group, 1-pyrrolyl group, 2-pyrrolyl group, 3-pyrrolyl group, 1-imidazolyl group, 2-imidazolyl group, 4-imidazolyl group, 1-pyrazolyl group, 3-pyrazolyl group, 4-pyrazolyl group, 2-thiazolyl group, 4-thiazolyl group, 5-thiazolyl group, 3-isothiazolyl group, 4-isothiazolyl group, 5-isothiazolyl group, 2-oxazolyl group, 4-oxazolyl group, 5-oxazolyl group, 3-isooxazolyl group, 4-isooxazolyl group, 5-isooxazolyl group, 2-pyridyl group, 3-pyridyl group, 4-pyridyl group, 2-pyradinyl group, 2-pyrimidinyl group, 4-pyrimidinyl group, 5-pyrimidinyl group, 3-pyridazinyl group, 4-pyridazinyl group, 1-indolizinyl group, 2-indolizinyl group, 3-indolizinyl group, 5-indolizinyl group, 6-indolizinyl group, 7-indolizinyl group, 8-indolizinyl group, 1-isoindolyl group, 4-isoindolyl group, 5-isoindolyl group, 1-indolyl group, 2-indolyl group, 3-indolyl group, 4-indolyl group, 5-indolyl group, 6-indolyl group, 7-indolyl group, 1-indazolyl group, 2-indazolyl group, 3-indazolyl group, 4-indazolyl group, 5-indazolyl group, 6-indazolyl group, 7-indazolyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 1-phthalazinyl group, 5-phthalazinyl group, 6-phthalazinyl group, 2-naphthyridinyl group, 3-naphthyridinyl group, 4-naphthyridinyl group, 2-quinoxalinyl group, 5-quinoxalinyl group, 6-quinoxalinyl group, 2-quinazolinyl group, 4-quinazolinyl group, 5-quinazolinyl group, 6-quinazolinyl group, 7-quinazolinyl group, 8-quinazolinyl group and the like.

Preferably, 2-pyridyl group, 3-pyridyl group and 4-pyridyl group may be mentioned.

Examples of $C_{3-6}$ cycloalkyl group are such as cyclopropyl, cyclobutyl, cyclopentyl, cyclohexyl, cycloheptyl, cyclooctyl and the like.

Preferably, cyclopropyl, cyclobutyl and cyclohexyl may be mentioned.

Examples of $C_{1-6}$ alkylamino group are such as methylamino, ethylamino, n-propylamino, i-propylamino, c-propylamino, n-butylamino, i-butylamino, s-butylamino, t-butylamino, c-butylamino, 1-pentylamino, 2-pentylamino, 3-pentylamino, i-pentylamino, neopentylamino, t-pentylamino, c-pentylamino, 1-hexylamino, 2-hexylamino, 3-hexylamino, c-hexylamino, 1-methyl-n-pentylamino, 1,1,2-trimethyl-n-propylamino, 1,2,2-trimethyl-n-propylamino, 3,3-dimethyl-n-butylamino and the like.

Preferably, methylamino, ethylamino, n-propylamino, i-propylamino and n-butylamino may be mentioned.

Examples of di-$C_{1-6}$ alkylamino group are such as dimethylamino, diethylamino, di-n-propylamino, di-i-propylamino, di-c-propylamino, di-n-butylamino, di-i-butylamino, di-s-butylamino, di-t-butylamino, di-c-butylamino, di-1-pentylamino, di-2-pentylamino, di-3-pentylamino, di-i-pentylamino, di-neopentylamino, di-t-pentylamino, di-c-pentylamino, di-1-hexylamino, di-2-hexylamino, di-3-hexylamino, di-c-hexylamino, di-(1-methyl-n-pentyl)amino, di-(1,1,2-trimethyl-n-propyl)amino, di-(1,2,2-trimethyl-n-propyl)amino, di-(3,3-dimethyl-n-butyl)amino, methyl(ethyl)amino, methyl(n-propyl) amino, methyl(i-propyl)amino, methyl(c-propyl)amino, methyl(n-butyl) amino, methyl(i-butyl) amino, methyl(s-butyl)amino, methyl(t-butyl)amino, methyl(c-butyl)amino, ethyl( n-propyl)amino, ethyl(i-propyl)amino, ethyl(c-propyl)amino, ethyl(n-butyl) amino, ethyl(i-butyl)amino, ethyl(s-butyl)amino, ethyl(t-butyl)amino, ethyl(c-butyl)amino, n-propyl(i-propyl)amino, n-propyl(c-propyl)amino, n-propyl(n-butyl)amino, n-propyl(i-butyl)amino, n-propyl(s-butyl)amino, n-propyl(t-butyl) amino, n-propyl(c-butyl)amino, i-propyl(c-propyl)amino, i-propyl(n-butyl)amino, i-propyl(i-butyl)amino, i-propyl(s-butyl)amino, i-propyl(t-butyl)amino, i-propyl(c-butyl) amino, c-propyl(n-butyl)amino, c-propyl(i-butyl)amino, c-propyl(s-butyl)amino, c-propyl(t-butyl)amino, c-propyl(c-butyl)amino, n-butyl(i-butyl)amino, n-butyl(s-butyl)amino, n-butyl(t-butyl)amino, n-butyl(c-butyl)amino, i-butyl(s-butyl)amino, i-butyl(t-butyl)amino, i-butyl(c-butyl)amino, s-butyl(t-butyl)amino, s-butyl(c-butyl)amino, t-butyl(c-butyl)amino and the like.

Preferably, dimethylamino, diethylamino, di-n-propylamino, di-i-propylamino and di-n-butylamino may be mentioned.

Examples of $C_{1-6}$ alkylcarbonylamino group are such as methylcarbonylamino, ethylcarbonylamino, n-propylcarbonylamino, i-propylcarbonylamino, n-butylcarbonylamino, i-butylcarbonylamino, s-butylcarbonylamino, t-butylcarbonylamino, 1-pentylcarbonylamino, 2-pentylcarbonylamino, 3-penylcarbonylamino, i-pentylcarbonylamino, neopentylcarbonylamino, t-pentylcarbonylamino, 1-hexylcarbonylamino, 2-hexylcarbonylamino, 3-hexylcarbonylamino and the like.

Preferably, methylcarbonylamino, ethylcarbonylamino, n-propylcarbonylamino, i-propylcarbonylamino and n-butylcarbonylamino may be mentioned.

Examples of $C_{1-6}$ alkylsulfonylamino group are such as methylsulfonylamino, ethylsulfonylamino, n-propylsulfonylamino, i-propylsulfonylamino, n-butylsulfonylamino, i-butylsulfonylamino, s-butylsulfonylamino, t-butylsulfonylamino, 1-pentylsulfonylamino, 2-pentylsulfonylamino, 3-pentylsulfonylamino, i-pentylsulfonylamino, neopentylsulfonylamino, t-pentylsulfonylamino, 1-hexylsulfonylamino, 2-hexylsulfonylamino, 3-hexylsulfonylamino and the like.

Preferably, methylsulfonylamino, ethylsulfonylamino, n-propylsulfonylamino, i-propylsulfonylamino and n-butylsulfonylamino may be mentioned.

Examples of $C_{1-6}$ alkylaminocarbonyl group are such as methylaminocarbonyl, ethylaminocarbonyl, n-propylaminocarbonyl, i-propylaminocarbonyl, n-butylaminocarbonyl, i-butylaminocarbonyl, s-butylaminocarbonyl, t-butylaminocarbonyl, 1-pentylaminocarbonyl, 2-pentylaminocarbonyl, 3-pentyl-aminocarbonyl, i-pentylaminocarbonyl, neopentylaminocarbonyl, t-pentylaminocarbonyl, 1-hexylaminocarbonyl, 2-hexylaminocarbonyl, 3-hexylaminocarbonyl and the like.

Preferably, methylaminocarbonyl, ethylaminocarbonyl, n-propylaminocarbonyl, i-propylaminocarbonyl and n-butylaminocarbonyl may be mentioned.

Examples of di-$C_{1-6}$ alkylaminocarbonyl group are such as dimethylaminocarbonyl, diethylaminocarbonyl, di-n-propylaminocarbonyl, di-i-propylaminocarbonyl, di-c-propylaminocarbonyl, di-n-butylaminocarbonyl, di-i-butylaminocarbonyl, di-s-butylaminocarbonyl, di-t-butylaminocarbonyl, di-c-butylaminocarbonyl, di-1-pentylaminocarbonyl, di-2-pentylaminocarbonyl, di-3-pentylaminocarbonyl, di-i-pentylaminocarbonyl, di-neopentylaminocarbonyl, di-t-pentylaminocarbonyl, di-c-pentylaminocarbonyl, di-1-hexylaminocarbonyl, di-2-hexylaminocarbonyl, di-3-hexylaminocarbonyl and the like.

Preferably, dimethylaminocarbonyl, diethylaminocarbonyl, di-n-propylaminocarbonyl, di-i-propylaminocarbonyl, di-c-propylaminocarbonyl and di-n-butyl-aminocarbonyl may be mentioned.

Examples of $C_{1-6}$ alkylcarbonyl group are such as methylcarbonyl, ethylcarbonyl, n-propylcarbonyl, i-propylcarbonyl, n-butylcarbonyl, i-butylcarbonyl, s-butylcarbonyl, t-butylcarbonyl, 1-pentylcarbonyl, 2-pentylcarbonyl, 3-pentylcarbonyl, i-pentylcarbonyl, neopentylcarbonyl, t-pentylcarbonyl, 1-hexylcarbonyl, 2-hexylcarbonyl, 3-hexylcarbonyl and the like.

Preferably, methylcarbonyl, ethylcarbonyl, n-propylcarbonyl, i-propylcarbonyl and n-butylcarbonyl may be mentioned.

Examples of $C_{1-6}$ alkoxycarbonyl group are such as methoxycarbonyl, ethoxycarbonyl, n-propoxycarbonyl, i-propoxycarbonyl, n-butoxycarbonyl, i-butoxycarbonyl, s-butoxycarbonyl, t-butoxycarbonyl, 1-pentyloxycarbonyl, 2-pentyloxycarbonyl, 3-pentyloxycarbonyl, i-pentyloxycarbonyl, neopentyloxy-carbonyl, t-pentyloxycarbonyl, 1-hexyloxycarbonyl, 2-hexyloxycarbonyl, 3-hexyloxycarbonyl and the like.

Preferably, methoxycarbonyl, ethoxycarbonyl, n-propoxycarbonyl, i-propoxycarbonyl, n-butoxycarbonyl, i-butoxycarbonyl, s-butoxycarbonyl and t-butoxycarbonyl may be mentioned.

Examples of $C_{1-6}$ alkylsulfonyl group are such as methanesulfonyl, ethanesulfonyl and the like.

Examples of straight-chain $C_{5-8}$ alkyl group are such as n-pentyl group, 5-hydroxy-n-pentyl group, 5-trifluoro-n-pentyl group, n-hexyl group, 6-hydroxy-n-hexyl group, 6-trifluoro-n-hexyl group, n-heptyl group, n-octyl group and the like.

Preferably, n-pentyl group, n-hexyl group may be mentioned.

As preferable compounds used in the present invention, the following compounds may be mentioned.

(1) The benzopyran derivative of the formula (1) or the formula (2), or the pharmaceutically acceptable salt thereof, wherein both $R^1$ and $R^2$ represent methyl group, $R^3$ represents a hydroxyl group and $R^4$ represents hydrogen atom.

(2) The benzopyran derivative or the pharmaceutically acceptable salt thereof described in (1) above, wherein $R^5$ represents $C_{1-6}$ alkyl group substituted with $C_{6-14}$ aryl group.

(3) The benzopyran derivative or the pharmaceutically acceptable salt thereof described in (2) above, wherein $R^6$ represents nitro group.

(4) The benzopyran derivative of the formula (2) or the pharmaceutically acceptable salt thereof described in (3) above.

(5) The benzopyran derivative or the pharmaceutically acceptable salt thereof described in (2) above, wherein $R^6$ represents $C(O)NH_2$.

(6) The benzopyran derivative or the pharmaceutically acceptable salt thereof described in (2) above, wherein $R^6$ represents methyl group.

Concrete examples of the compounds that can be used in the present invention are shown below, but the present invention is not limited thereto. In addition, "Me" means methyl group, "Et" means ethyl group, "Pr" means propyl group, "Bu" means butyl group, "Pen" means pentyl group, "Hex" means hexyl group, "Ph" means phenyl group, "o" means "ortho", "m" means "meta" and "p" means "para", respectively.

TABLE 1

| $R^1$ | $R^2$ | $R^3$ | $R^4$ | n |
|---|---|---|---|---|
| H | H | OH | H | 0 |
| Me | Me | OH | Me | 1 |
| Me | Me | OH | Et | 2 |
| Me | Me | OH | n-Pr | 3 |
| Me | Me | OH | i-Pr | 4 |
| Me | Me | OH | n-Bu | 0 |
| Me | Me | OH | i-Bu | 1 |
| Me | Me | OH | t-Bu | 2 |

TABLE 1-continued

Structure A: 4-[N-R⁴-N-(CH₂)ₙ-Ph]amino-chroman with H₂NOC- at 6-position, R¹ on C2, R² on C2, R³ on C3

Structure B: same as A but H₂NOC- at 7-position

| R¹ | R² | R³ | R⁴ | n |
|---|---|---|---|---|
| Me | Me | OH | n-Pen | 3 |
| Me | Me | OH | n-Hex | 4 |
| Me | Me | OH | H | 2 |
| Me | Me | OH | Me | 2 |
| Me | Me | OH | Et | 3 |
| Me | Me | OCOMe | H | 2 |
| Me | Me | OCOEt | H | 2 |
| Me | Me | OH | H | 1 |
| Me | Me | OH | H | 2 |
| Me | Me | OH | H | 3 |
| Me | Me | OH | H | 4 |
| Et | Et | OH | H | 2 |
| n-Pr | n-Pr | OH | H | 2 |
| i-Pr | i-Pr | OH | H | 2 |
| n-Bu | n-Bu | OH | H | 2 |
| i-Bu | i-Bu | OH | H | 2 |
| t-Bu | t-Bu | OH | H | 3 |
| n-Pen | n-Pen | OH | H | 3 |
| n-Hex | n-Hex | OH | H | 3 |
| CF₃ | CF₃ | OH | H | 3 |
| CH₂OCH₃ | CH₂OCH₃ | OH | H | 3 |

TABLE 2

Structure A: 4-[N-R⁴-N-(CH₂)ₙ-Ph]amino-chroman with O₂N- at 6-position

Structure B: same as A but O₂N- at 7-position

| R¹ | R² | R³ | R⁴ | n |
|---|---|---|---|---|
| H | H | OH | H | 0 |
| Me | Me | OH | Me | 1 |
| Me | Me | OH | Et | 2 |
| Me | Me | OH | n-Pr | 3 |
| Me | Me | OH | i-Pr | 4 |
| Me | Me | OH | n-Bu | 0 |
| Me | Me | OH | i-Bu | 1 |
| Me | Me | OH | t-Bu | 2 |
| Me | Me | OH | n-Pen | 3 |
| Me | Me | OH | n-Hex | 4 |
| Me | Me | OH | H | 2 |

TABLE 2-continued

| R¹ | R² | R³ | R⁴ | n |
|---|---|---|---|---|
| Me | Me | OH | Me | 2 |
| Me | Me | OH | Et | 3 |
| Me | Me | OCOMe | H | 2 |
| Me | Me | OCOEt | H | 2 |
| Me | Me | OH | H | 1 |
| Me | Me | OH | H | 2 |
| Me | Me | OH | H | 3 |
| Me | Me | OH | H | 4 |
| Et | Et | OH | H | 2 |
| n-Pr | n-Pr | OH | H | 2 |
| i-Pr | i-Pr | OH | H | 2 |
| n-Bu | n-Bu | OH | H | 2 |
| i-Bu | i-Bu | OH | H | 2 |
| t-Bu | t-Bu | OH | H | 3 |
| n-Pen | n-Pen | OH | H | 3 |
| n-Hex | n-Hex | OH | H | 3 |
| CF₃ | CF₃ | OH | H | 3 |
| CH₂OCH₃ | CH₂OCH₃ | OH | H | 3 |

TABLE 3

Structure A: 4-[N-R⁴-N-(CH₂)ₙ-Ph]amino-chroman with Me- at 6-position

Structure B: same as A but Me- at 7-position

| R¹ | R² | R³ | R⁴ | n |
|---|---|---|---|---|
| H | H | OH | H | 0 |
| Me | Me | OH | Me | 1 |
| Me | Me | OH | Et | 2 |
| Me | Me | OH | n-Pr | 3 |
| Me | Me | OH | i-Pr | 4 |
| Me | Me | OH | n-Bu | 0 |
| Me | Me | OH | i-Bu | 1 |
| Me | Me | OH | t-Bu | 2 |
| Me | Me | OH | n-Pen | 3 |
| Me | Me | OH | n-Hex | 4 |
| Me | Me | OH | H | 2 |
| Me | Me | OH | Me | 2 |
| Me | Me | OH | Et | 3 |
| Me | Me | OCOMe | H | 2 |

TABLE 3-continued

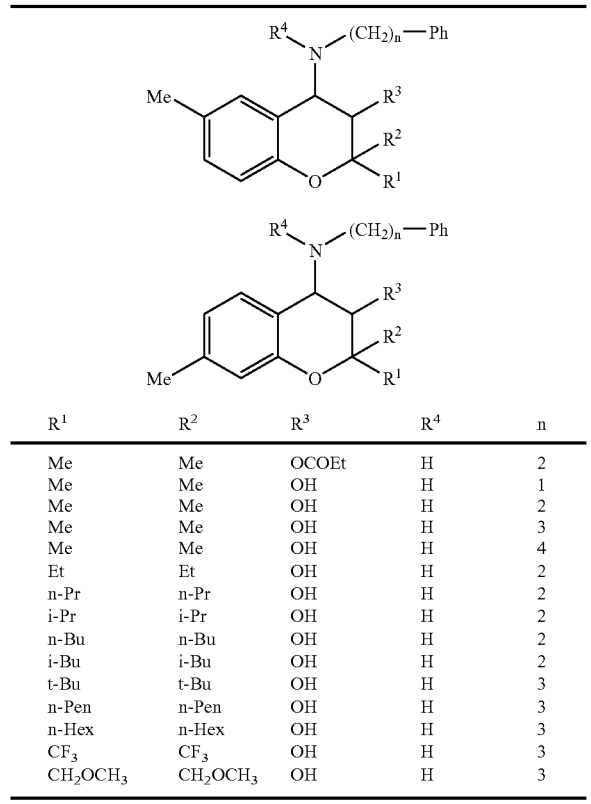

| R¹ | R² | R³ | R⁴ | n |
|---|---|---|---|---|
| Me | Me | OCOEt | H | 2 |
| Me | Me | OH | H | 1 |
| Me | Me | OH | H | 2 |
| Me | Me | OH | H | 3 |
| Me | Me | OH | H | 4 |
| Et | Et | OH | H | 2 |
| n-Pr | n-Pr | OH | H | 2 |
| i-Pr | i-Pr | OH | H | 2 |
| n-Bu | n-Bu | OH | H | 2 |
| i-Bu | i-Bu | OH | H | 2 |
| t-Bu | t-Bu | OH | H | 3 |
| n-Pen | n-Pen | OH | H | 3 |
| n-Hex | n-Hex | OH | H | 3 |
| CF₃ | CF₃ | OH | H | 3 |
| CH₂OCH₃ | CH₂OCH₃ | OH | H | 3 |

TABLE 4

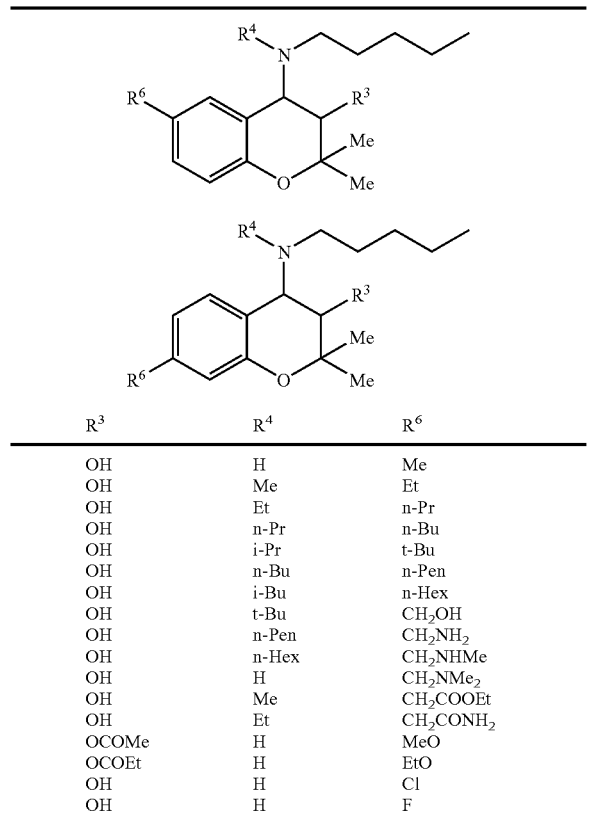

| R³ | R⁴ | R⁶ |
|---|---|---|
| OH | H | Me |
| OH | Me | Et |
| OH | Et | n-Pr |
| OH | n-Pr | n-Bu |
| OH | i-Pr | t-Bu |
| OH | n-Bu | n-Pen |
| OH | i-Bu | n-Hex |
| OH | t-Bu | CH₂OH |
| OH | n-Pen | CH₂NH₂ |
| OH | n-Hex | CH₂NHMe |
| OH | H | CH₂NMe₂ |
| OH | Me | CH₂COOEt |
| OH | Et | CH₂CONH₂ |
| OCOMe | H | MeO |
| OCOEt | H | EtO |
| OH | H | Cl |
| OH | H | F |

TABLE 4-continued

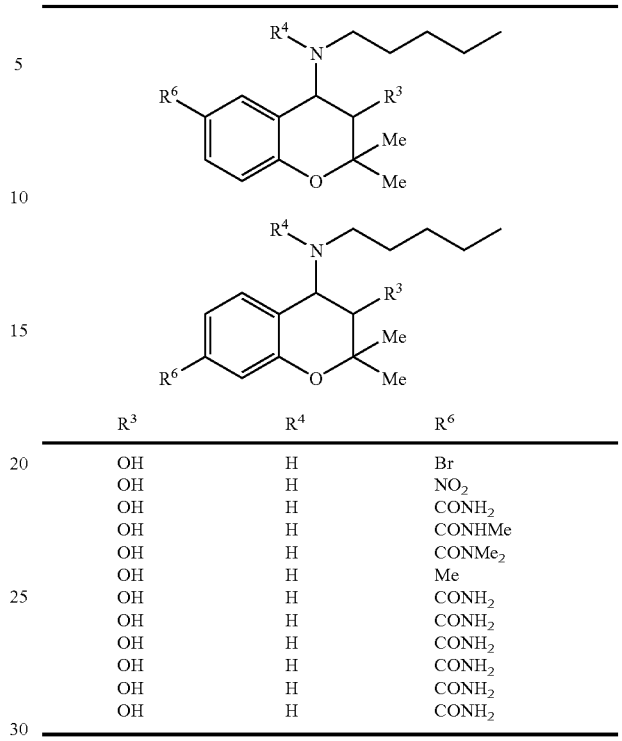

| R³ | R⁴ | R⁶ |
|---|---|---|
| OH | H | Br |
| OH | H | NO₂ |
| OH | H | CONH₂ |
| OH | H | CONHMe |
| OH | H | CONMe₂ |
| OH | H | Me |
| OH | H | CONH₂ |
| OH | H | CONH₂ |
| OH | H | CONH₂ |
| OH | H | CONH₂ |
| OH | H | CONH₂ |
| OH | H | CONH₂ |

TABLE 5

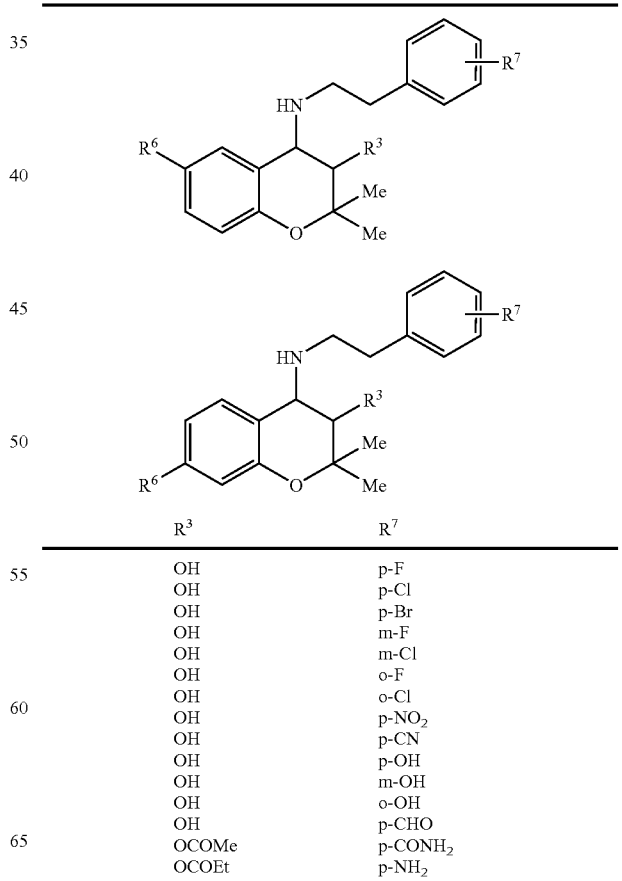

| R³ | R⁷ |
|---|---|
| OH | p-F |
| OH | p-Cl |
| OH | p-Br |
| OH | m-F |
| OH | m-Cl |
| OH | o-F |
| OH | o-Cl |
| OH | p-NO₂ |
| OH | p-CN |
| OH | p-OH |
| OH | m-OH |
| OH | o-OH |
| OH | p-CHO |
| OCOMe | p-CONH₂ |
| OCOEt | p-NH₂ |

TABLE 5-continued

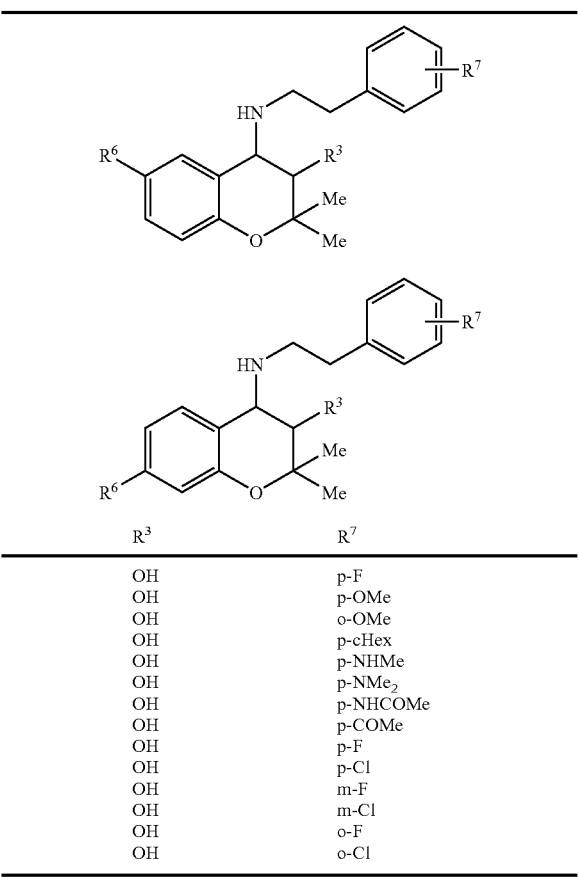

| R³ | R⁷ |
|---|---|
| OH | p-F |
| OH | p-OMe |
| OH | o-OMe |
| OH | p-cHex |
| OH | p-NHMe |
| OH | p-NMe₂ |
| OH | p-NHCOMe |
| OH | p-COMe |
| OH | p-F |
| OH | p-Cl |
| OH | m-F |
| OH | m-Cl |
| OH | o-F |
| OH | o-Cl |

The compound according to the present invention has asymmetric carbon atoms at 3-position and 4-position, thus optical isomers thereof based on the asymmetric carbon atoms are present, and optical active substances can be also used in the application of the present invention, like racemic modifications. Further, cis- and trans-isomer based on configuration at 3-position and 4-position may be included, but trans-isomer is preferred.

Further, when the compounds can form their salts, the pharmaceutically acceptable salts thereof can also be used as active ingredients.

Examples of pharmaceutically acceptable salt are such as hydrochlorides, hydrobromides, sulfates, methanesulfonates, acetates, benzoates, tartrates, phosphates, lactates, maleates, fumarates, malates, gluconates, salicylates and the like.

Preferably, hydrochlorides, methanesulfonates and maleates may be mentioned.

The method of preparation of the compound according to the present invention is illustrated.

The compound of the formula (1) or the formula (2) can be obtained by reacting compound of the formula (3) or the formula (4) with the compound (5) in an inert solvent as shown in the reaction scheme described below.

The compound of the formula (3) or the formula (4) can be synthesized according to known methods (methods described in J. M. Evans et al., J. Med. Chem. 1984, 27, 1127; J. Med. Chem. 1986, 29, 2194; J. T. North et al., J. Org. Chem. 1995, 60, 3397, as well as Jananese Patent Application Laid-open No. Sho 56-57785, Jananese Patent Application Laid-open No. Sho 56-57786, Jananese Patent Application Laid-open No. Sho 58-188880, Jananese Patent Application Laid-open No. Hei 2-141, Jananese Patent Application Laid-open No. Hei 10-87650 and Jananese Patent Application Laid-open No. Hei 11-209366 and the like.).

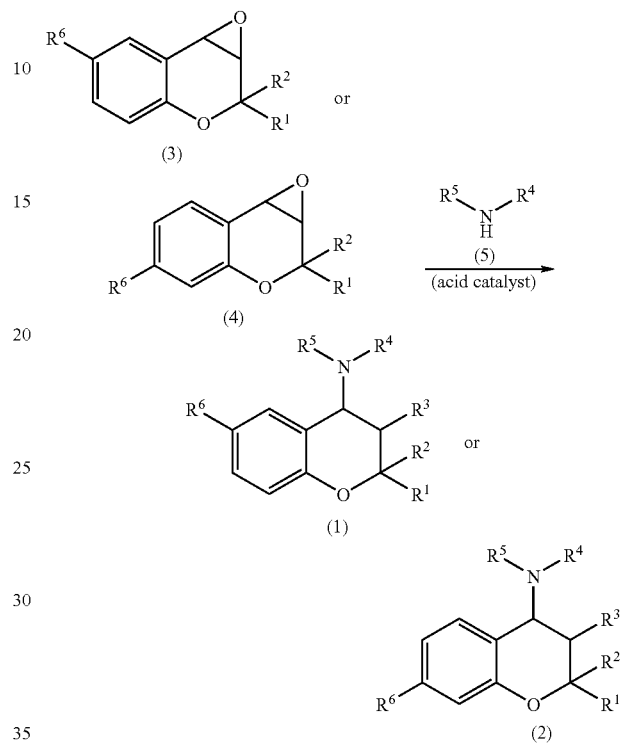

As the solvents used in the reaction of the compound of the formula (3) or the formula (4) with the compound (5), the following may be mentioned.

Sulfoxide type solvents exemplified by dimethylsulfoxide; amide type solvents exemplified by dimethylformamide or dimethylacetamide; ether type solvents exemplified by ethylether, dimethoxyethane or tetrahydrofuran; halogen type solvents exemplified by dichloromethane, chloroform and dichloroethane; nitrile type solvents exemplified by acetonitrile and propionitrile; aromatic hydrocarbon type solvents exemplified by benzene and toluene; hydrocarbon type solvents exemplified by hexane and heptane; and ester type solvents exemplified by ethyl acetate may be mentioned. Further, the reaction can be carried out in the absence of any solvent. Preferably, ether type solvents and nitrile type solvents may be mentioned.

The reaction temperature is generally from −80° C. to the reflux temperature of the reaction solvent, preferably from −10° C. to 100° C.

The molar ratio of the reaction materials is within the range of 0.5–20.0, preferably 1.0–10.0, for the compound (5)/the compound (3) or the compound (5)/the compound (4).

An acid catalyst may be used in the reaction.

Examples of the acid catalysts used are such as inorganic acids exemplified by hydrochloric acid and sulfuric acid, and Lewis acids exemplified by aluminum chloride, titanium tetrachloride, boron trifluoride diethyl ether complex, perchloric acid, lithium perchlorate, lithium bromide and ytterbium trifluoromethanesulfonate and the like may be mentioned.

Preferably, lithium bromide, perchloric acid and lithium perchlorate may be mentioned.

The compounds of the formula (2) can be obtained upon diazotization of the compound of the formula (6) followed by reductive deamination reaction as shown in the reaction scheme described below (the method described in Jananese Patent Application Laid-open No. Sho 52-91866).

The compounds of the formula (6) can be synthesized according to known methods (methods described in J. M. Evans et al., J. Med. Chem. 1984, 27, 1127; J. Med. Chem. 1986, 29, 2194; as well as Jananese Patent Application Laid-open No. Sho 56-57785, Jananese Patent Application Laid-open No. Sho 56-57786, Jananese Patent Application Laid-open No. Sho 58-188880, Jananese Patent Application Laid-open No. Hei 2-141, Jananese Patent Application Laid-open No. Hei 10-87650 and Jananese Patent Application Laid-open No. Hei 11-209366, Jananese Patent Application Laid-open No. 2001-151767 and the like.).

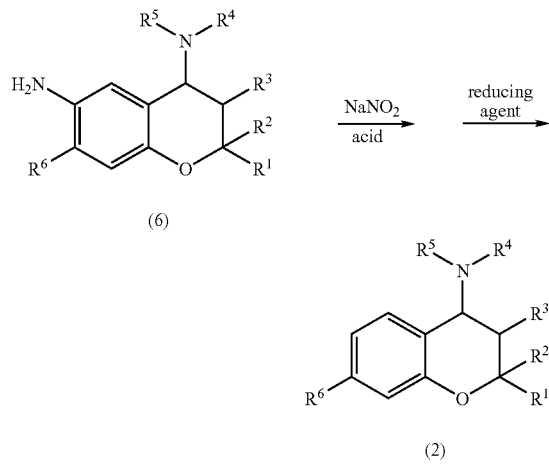

Examples of acid to be used in diazotization are such as hydrochloric acid, sulfuric acid and the like.

Examples of reducing agent to be used in reductive deamination reaction of diazonium salt are such as alcohol exemplified by methanol and ethanol, hypophosphorous acid, sodium borohydride and the like, but preferred is hypophosphorous acid.

Syntheses of optically active compounds among the compounds of the formula (1) or the formula (2) can be attained by utilizing optical resolution methods (Jananese Patent Application Laid-open No. Hei 3-141286, U.S. Pat. No. 5,097,037 and European Patent No. 409,165).

Furthermore, syntheses of optically active compounds of the formula (3) or the formula (4) can be attained by utilizing asymmetric synthetic methods (Jananese National Publication No. Hei 5-507645, Jananese Patent Application Laid-open No. Hei 5-301878, Jananese Patent Application Laid-open No. Hei 7-285983, European Patent Laid-open No. 535377 and U.S. Pat. No. 5,420,314).

As described above, the inventors of the present invention found that the compound of the formula (1) or the formula (2) has the strong prolongation effect on the refractory period. The prolongation effect on the refractory period is one of mechanisms of anti-arrhythmic action and is an important indicator that can be taken in judging the effectiveness in clinical arrhythmia. Conventional anti-arrhythmic agents having the prolongation effect on the refractory period as the main mechanism (such as d-sotalol belonging to Class III of the antiarrhythmic agent classification according to Vaughan Williams) have been the therapeutic problems in inducing highly dangerous arrhythmia leading to the sudden death from such as torsades de pointes among others due to prolongation of action potential in ventricular muscle correlated to the prolongation effect on the refractory period, and thus becoming the therapeutic problem in arrhythmia mainly of atrial muscle (such as supraventricular tachycardia, atrial flutter, atrial fibrillation and the like).

In order to solve the problems, the inventors of the present invention carried out the investigation of compounds having the prolongation effect on the refractory period selective for atrium muscle than for ventricular muscle, and found that the compound of the formula (1) or the formula (2) has the prolongation effect on the refractory period selective for atrium muscle without any influence on the refractory period and action potential in ventricular muscle. The difference between the findings by the inventors of the present invention and the prior art is in providing the prolongation effect on the refractory period selective for atrium muscle to these compound group, which may be shown by the facts that there is no influence on the action potential duration period of isolated ventricular muscle and there is no influence on QT in the electrocardiogram of anesthetized animal. From above, the compounds of the present invention show no inducing action of arrhythmia in ventricular muscle, thus they can contribute to much safer use in arrhythmia mainly of atrial muscle in comparison with the prior art. The present technical knowledge is beneficial for therapeutic or preventive uses as anti-atrial fibrillation agents, anti-atrial flutter agents and anti-atrial tachycardia agents relating to paroxysmal, chronic, preoperative, intraoperative or postoperative atrial arrhythmia, prevention in the progression leading to embolus due to arrhythmia of artial nature, prevention in the progression leading to ventricular arrhythmia or tachycardia from atrial arrhythmia or tachycardia, and averting the life threatening prognosis due to preventive action on atrial arrhythmia or tachycardia leading to ventricular arrhythmia or tachycardia.

The present invention provides a pharmaceutical composition or a veterinary pharmaceutical composition containing a compound of the formula (1) or the formula (2) in an effective amount for these treatments.

As forms of administration for the compound according to the present invention, parenteral administration forms such as injections (subcutaneous, intravenous, intramuscular and intraperitoneal injections), ointments, suppositories, aerosols and the like, and oral administration forms such as tablets, capsules, granules, pills, syrups, solutions, emulsions, suspensions and the like can be mentioned.

The pharmaceutical or veterinary pharmaceutical composition described above contains the compound according to the present invention in an amount of about 0.01–99.5%, preferably about 0.1–30%, based on the total weight of the composition.

In addition to the compound according to the present invention or the composition containing the compound, other pharmaceutically or veterinary pharmaceutically active compounds may be contained.

Further, these compositions may contain the plurality of compounds according to the present invention.

An amount of the compound according to the present invention to be used in clinical administration may vary depending on age, weight and sensitivity of the patient, symptomatic condition and the like, but an effective amount in clinical administration is generally about 0.003–1.5 g, preferably 0.01–0.6 g, per day for adult. If necessary, however, the amount outside of the aforementioned range may be used.

The compound according to the present invention is formulated for administration by conventional pharmaceutical means.

That is, tablets, capsules, granules and pills for oral administration are prepared by using excipients such as sucrose, lactose, glucose, starch and mannitol; binders such as hydroxypropyl cellulose, syrup, gum arabic, gelatin, sorbitol, tragacanth, methyl cellulose and polyvinyl pyrrolidone; disintegrators such as starch, carboxymethyl cellulose or its calcium salt, microcrystalline cellulose and polyethylene glycol; lubricants such as talc, magnesium or calcium stearate, and silica; lubricating agents such as sodium laurate and glycerol and the like.

Injections, solutions, emulsions, suspensions, syrups and aerosols are prepared by using solvents for the active components such as water, ethyl alcohol, isopropyl alcohol, propylene glycol, 1,3-butylene glycol and polyethylene glycol; surfactants such as sorbitan fatty acid ester, polyoxyethylene sorbitan fatty acid ester, polyoxyethylene fatty acid ester, polyoxyethylene ether of hydrogenated castor oil and lecithin; suspending agents such as carboxymethyl sodium salt, cellulose derivatives such as methyl cellulose, tragacanth, and natural rubbers such as gum arabic; and preserves such as p-hydroxybenzoic acid esters, benzalkonium chloride and sorbic acid salts and the like.

For ointments that are transdermally adsorptive pharmaceutics, for example, white vaseline, liquid paraffin, higher alcohols, Macrogol ointments, hydrophilic ointments, aqueous gel-type bases and the like are used.

Suppositories are prepared by using, for example, cocoa fats, polyethylene glycol, lanolin, fatty acid triglyceride, coconut oil, polysorbate and the like.

BEST MODE FOR CARRYING OUT THE INVENTION

The present invention is illustrated in detail by the Examples as follows, but the present invention is not limited to these Examples.

Furthermore, salen manganese complex means an optically active compound of the formula below which was synthesized according to the method similar to one described in Jananese Patent Application Laid-open No. Hei 7-285983.

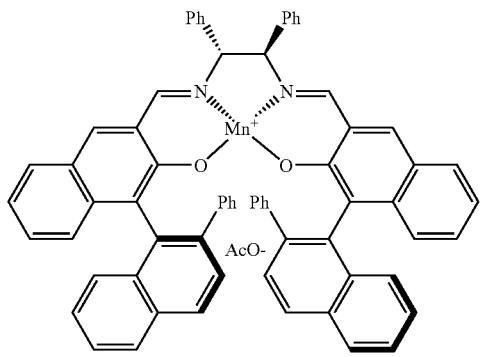

In addition, (3R*,4S*)-6-amino-3,4-dihydro-2,2-dimethyl-7-nitro-4-(2'-phenethylamino)-2H-1-benzopyran-3-ol used as the raw material in Synthetic Example 6 was prepared by heating the compound synthesized according to the method described in Jananese Patent Application Laid-open No. 2001-151767 (Synthetic Example 72) in ethanol and 35% hydrochloric acid.

SYNTHESIS EXAMPLES

Reference Synthesis Example 1

(3R*,4R*)-6-cyano-3,4-epoxy-3,4-dihydro-2,2-dimethyl-2H-1-benzopyran

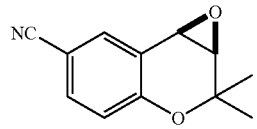

To a solution (34 mL) of ethyl acetate containing 3.4 g (18 mmol) of 6-cyano-2,2-dimethyl-2H-1-benzopyran (synthesized according to the method described in SYNTHESIS, 1995, 707), salen manganese complex (0.56 g, 0.54 mmol), 4-(3-phenylpropyl)-pyridineoxide) (0.42 g, 1.8 mmol) and aqueous sodium hypochlorite solution (21 g, 12.8% wt., 36 mmol) were added at room temperature, and then stirred for one hour at room temperature. After Celite filtration upon addition of water, organic phase was separated, washed with aqueous saturated sodium chloride solution, and dried over anhydride sodium sulfate. After distilling off the solvent, the residue was purified by silica gel column chromatography (hexane:acetone=5:1), and then re-crystallized from ethyl acetate-hexane to obtain 2.05 g of the intended compound in light brown crystal (Yield 57%).

$^1$H-NMR (CDCl$_3$) δ: 1.30 (s, 3H), 1.60 (s, 3H), 3.54 (d, J=4.3 Hz, 1 H), 3.91 (d, J=4.3 Hz, 1H), 6.87 (d, J=8.5 Hz, 1H), 7.53 (dd, J=1.9, 8.5 Hz, 1H), 7.65 (d, J=1.9 Hz, 1H). MS (EI) m/z: 145 (bp), 201 m.p. 145.3–146.6° C. $[\alpha]_D^{25}$=74.7 (c=1.0, CHCl$_3$)

Reference Synthesis Example 2

(3R*,4R*)-3,4-epoxy-6-ethyl-3,4-dihydro-2,2-dimethyl-2H-1-benzopyran

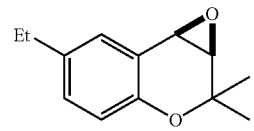

To a solution (2 mL) of ethyl acetate containing 100 mg (0.53 mmol) of 6-ethyl-2,2-dimethyl-2H-1-benzopyran (synthesized according to the method described in Jananese Patent Application Laid-open No. Sho 62-273972), salen manganese complex (17 mg, 0.016 mmol), 4-(3-phenylpropyl)-pyridineoxide) (12 mg, 0.053 mmol) and aqueous sodium hypochlorite solution (0.96 g, 1.14 Kg/mol, 1.1 mmol) were added at room temperature, and stirred for two hours at room temperature. After Celite filtration upon addition of water, organic phase was separated, washed with aqueous saturated sodium chloride solution, and dried over anhydride sodium sulfate. After distilling off the solvent, the residue was purified by silica gel column chromatography (chloroform) to obtain 75 mg of the intended compound in brown oily substance (Yield 69%).

¹H-NMR (CDCl₃) δ: 1.21–1.24 (m, 6H), 1.57 (s, 3H), 2.54–2.59 (m, 2H), 3.47 (d, J=4.4 Hz, 1 H), 3.87 (d, J=4.4 Hz, 1 H), 6.72 (d, J=8.2 Hz, 1 H), 7.66 (dd, J=2.2, 8.2 Hz, 1H), 7.20 (d, J=2.2 Hz, 1H).

Reference Synthesis Example 3

(3R*,4R*)-3,4-epoxy-3,4-dihydro-6-methyl-2,2-dimethyl-2H-1-benzopyran

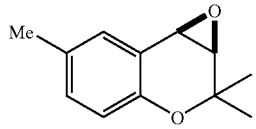

¹H-NMR (CDCl₃) δ: 1.23 (s, 3H), 1.57 (s, 3H), 2.28 (s, 3H), 3.47 (d, J=4.4 Hz, 1H), 3.85 (d, J=4.4 Hz, 1H), 6.69–7.14 (m, 3H). MS (EI) m/z: 135 (bp), 189 [M−1]⁺.

Reference Synthesis Example 4

(3R*,4S*)-6-cyano-4-(2-phenylethylamino)-3,4-dihydro-2,2-dimethyl-2H-1-benzopyran-3-ol

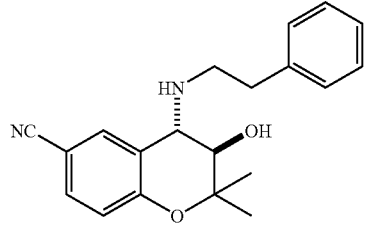

To a solution (13 mL) of acetonitrile containing the compound synthesized in Reference Synthesis Example 1 (1.3 g, 6.5 mmol) and lithium perchlorate (2.8 g, 26 mmol), 2-phenylethyl amine (3.3 mL, 26 mmol) was added at room temperature and stirred for one hour at 65° C. Upon addition of ethyl acetate, organic phase was washed with water and aqueous saturated sodium chloride solution, and then dried over anhydride sodium sulfate. After distilling off the solvent, the residue was purified by silica gel column chromatography (hexane:ethyl acetate=3:1) to obtain 1.88 g of the intended compound in brown oily substance (Yield 90%).

¹H-NMR (CDCl₃) δ: 1.18 (s, 3H), 1.49 (s, 3H), 2.76–2.97 (m, 5H), 3.50 (d, J=10.0 Hz, 1H), 3.63 (d, J=10.0 Hz, 1H), 6.81 (d, J=8.5 Hz, 1H), 7.22–7.41 (m, 7H). MS (EI) m/z: 202 (bp), 323 [M+1]⁺.

Reference Synthesis Example 5

(3R*,4S*)-6-cyano-4-[2-(4-fluorophenyl)ethylamino]-3,4-dihydro-2,2-dimethyl-2H-1-benzopyran-3-ol

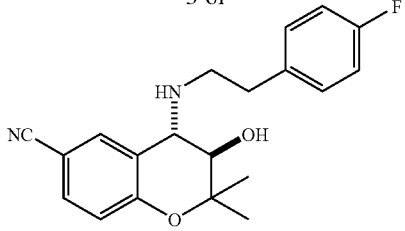

The compound was synthesized using 2-(4-fluorophenyl) ethylamine according to the method similar to one described in Reference Synthesis Example 4.

Yield 91%.

Brown Oily Substance.

¹H-NMR (CDCl₃) δ: 1.19 (s, 3H), 1.50 (s, 3H), 2.74–2.94 (m, 5H), 3.51 (d, J=10.1 Hz, 1H), 3.64 (d, J=10.1 Hz, 1H), 6.82 (d, J=8.5 Hz, 1H), 7.01–7.07 (m, 2H), 7.16–7.21 (m, 2H), 7.36–7.42 (m, 2H). MS (EI) m/z: 109, 132 (bp), 269, 340 [M]⁺.

Reference Synthesis Example 6

(3R*,4S*)-6-cyano-4-[2-(2-fluorophenyl)ethylamino]-3,4-dihydro-2,2-dimethyl-2H-1-benzopyran-3-ol

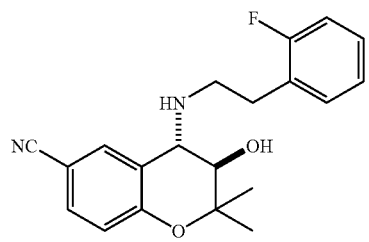

The compound was synthesized using 2-(2-fluorophenyl) ethylamine according to the method similar to one described in Reference Synthesis Example 4.

Yield 73%

Brown Oily Substance

¹H-NMR (CDCl₃) δ: 1.18 (s, 3H), 1.49 (s, 3H), 2.74–2.94 (m, 5H), 3.50 (d, J=10.0 Hz, 1H), 3.64 (d, J=10.0 Hz, 1H), 6.81 (d, J=8.5 Hz, 1H), 7.01–7.41 (m, 6H). MS (EI) m/z: 109, 160 (bp), 268, 341 [M+1]⁺.

Synthesis Example 1

(3R*,4S*)-4-[2-(4-chlorophenyl)ethylaminol]-6-ethyl-3,4-dihydro-2,2-dimethyl-2H-1-benzopyran-3-ol

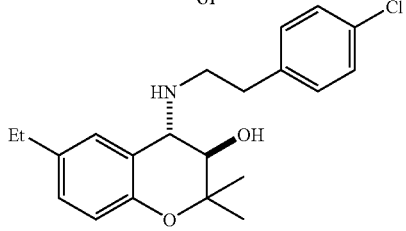

To a solution (0.30 mL) of acetonitrile containing the compound synthesized in Reference Synthesis Example 2 (59 mg, 0.29 mmol) and lithium perchlorate (0.38 g, 1.2 mmol), 2-(4-chlorophenyl) ethylamine (0.21 mL, 1.2 mmol) was added at room temperature and stirred for two hours at 65° C. Upon addition of ethyl acetate, organic phase was washed with water and aqueous saturated sodium chloride solution, and then dried over anhydride sodium sulfate. After distilling off the solvent, the residue was purified by silica gel column chromatography (chloroform:ethyl acetate=5:1) to obtain 36 mg of the intended compound in brown solid (Yield 34%).

¹H-NMR (CDCl₃) δ: 1.15–1.20 (m, 6H), 1.47 (s, 3H), 2.51 (q, J=7.7 Hz, 2H), 2.77–2.84 (m, 4H), 3.52 (d, J=10.0 Hz, 1H), 3.62 (d, J=10.0 Hz, 1H), 6.68–7.30 (m, 7H). MS (EI) m/z: 290 (bp), 341, 358 [M−1]⁺.

Synthesis Example 2

(3R*,4S*)-4-[2-(4-chlorophenyl)ethylamino]-3,4-dihydro-6-methyl-2,2-dimethyl-2H-1-benzopyran-3-ol

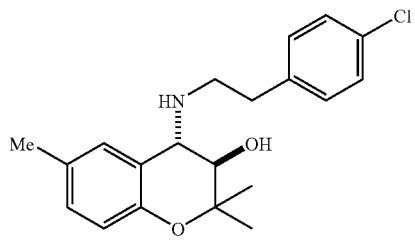

The compound was synthesized using the compound synthesized in Reference Synthesis Example 3 according to the method similar to one described in Synthesis Example 1.

Yield 60%

Colorless Crystal $^1$H-NMR (CDCl$_3$) δ: 1.16 (s, 3H), 1.47 (s, 3H), 2.22 (s, 3H), 2.77–2.83 (m, 5H), 3.50–3.59 (m, 2H), 6.66–7.28 (m, 7H). MS (FAB) m/z: 346 [M]$^+$ (bp). m.p. 133–135° C.

Synthesis Example 3

(3R*,4S*)-6-carbamoyl-4-(2-phenylethylamino)-3,4-dihydro-2,2-dimethyl-2H-1-benzopyran-3-ol

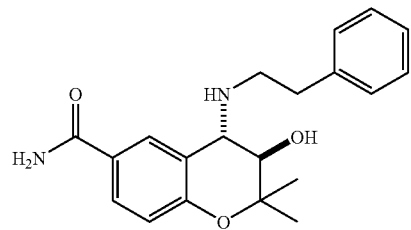

To a solution (7.2 mL) of dimethylsulfide containing the compound synthesized in Reference Synthesis Example 4 (1.44 g, 4.47 mmol) under ice-cooling, 30% aqueous hydrogen peroxide solution (1.44 mL) and potassium carbonate (93 mg, 0.67 mmol) were added and then stirred for 30 minutes at room temperature. Upon addition of a small amount of water, and then saturated sodium hydrogen carbonate, extracted with ethyl acetate and dried over anhydride sodium sulfate. After distilling off the solvent, the residue was re-crystallized from ethyl acetate-hexane solvent to obtain 1.28 g of the intended compound in colorless crystal (Yield 84%).

$^1$H-NMR (DMSO-d$_6$) δ: 1.10 (s, 3H), 1.37 (s, 3H), 2.72–2.83 (m, 4H), 3.54 (dd, J=5.2, 9.1 Hz, 1H), 3.64 (d, J=9.1 Hz, 1H), 5.27 (d, J=5.2 Hz, 1H), 6.72 (d, J=8.4 Hz, 1 H), 7.22–7.41 (m, 5H), 7.61 (dd, J=1.9, 8.4 Hz, 1H), 8.05 (d, J=1.9 Hz, 1H). MS (EI) m/z: 267 (bp), 341 [M+1]$^+$. m.p. 162.0–162.5° C.

Synthesis Example 4

(3R*,4S*)-6-carbamoyl-4-[2-(4-fluorophenyl)ethylamino]-3,4-dihydro-2,2-dimethyl-2H-1-benzopyran-3-ol

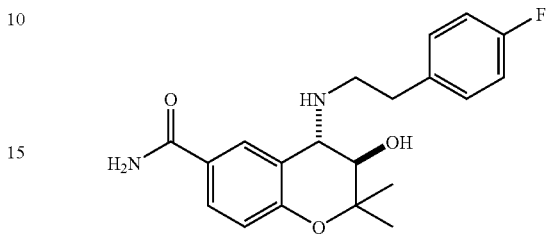

The compound was synthesized using the compound synthesized in Reference Synthesis Example 5 according to the method similar to one described in Synthesis Example 3.

Yield 79%

Colorless Crystal $^1$H-NMR (DMSO-d$_6$) δ: 1.10 (s, 3H), 1.37 (s, 3H), 2.54–2.83 (m, 4H), 3.54 (dd, J=5.1, 8.9 Hz, 1H), 3.63 (d, J=8.9 Hz, 1 H), 5.26 (d, J=5.1 Hz, 1H), 6.71 (d, J=8.3 Hz, 1H), 7.04–7.10 (m, 2H), 7.21–7.26 (m, 2H), 7.61 (dd, J=2.2, 8.3 Hz, 1H), 8.03 (d, J=2.2 Hz, 1H). MS (EI) m/z: 177 (bp), 286, 358 [M]$^+$. m.p. 186.5–189.3° C.

Synthesis Example 5

(3R*,4S*)-6-carbamoyl-4-[2-(4-fluorophenyl)ethylamino]-3,4-dihydro-2,2-dimethyl-2H-1-benzopyran-3-ol

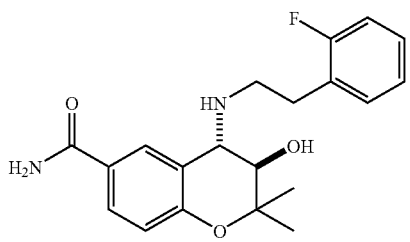

The compound was synthesized using the compound synthesized in Reference Synthesis Example 6 according to the method similar to one described in Synthesis Example 3.

Yield 34%

Colorless Crystal $^1$H-NMR (DMSO-d$_6$) δ: 1.10 (s, 3H), 1.36 (s, 3H), 2.20–2.80 (m, 4H), 3.54–3.63 (m, 2H), 5.27 (d, J=5.2 Hz, 1H), 6.71 (d, J=8.5 Hz, 1H), 7.07–7.29 (m, 4H), 7.61 (dd, J=8.5 Hz, 1H), 8.03 (s, 1H). MS (EI) m/z: 286 (bp), 359 [M+1]$^+$. m.p. 149.0–152.1° C.

Synthesis Example 6

(3R*,4S*)-3,4-dihydro-2,2-dimethyl-7-nitro-4-(2'-phenethylamino)-2H-1-benzopyran-3-ol maleate

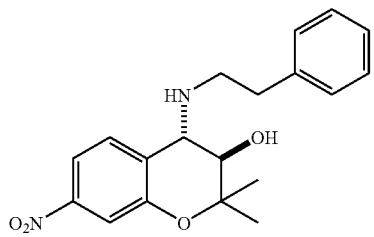

To a mixed solution of acetic acid (135 mL) and 4 mol/L hydrochloric acid (135 mL) containing (3R*,4S*)-6-amino-3,4-dihydro-2,2-dimethyl-7-nitro-4-(2'-phenethylamino)-2H-1-benzopyran-3-ol (45 g, 125.9 mmol), aqueous sodium nitrite solution (8.69 g, 125.9 mmol, dissolved in 45 mL water) was dropwise added at −20° C. over 30 minutes, followed by the dropwise addition of 50% phosphorous acid solution (225 mL). The temperature of the reaction solution was elevated to 0° C. and stirred for one hour. The reaction mixture was made to alkaline (pH 12) with 10 mol/L aqueous sodium hydroxide solution, extracted with ethyl acetate, then organic phase was washed with 1 mol/L aqueous sodium hydroxide, aqueous saturated ammonium chloride solution and aqueous saturated sodium chloride solution, and finally dried over anhydride sodium sulfate. After distilling off the solvent, the residue was purified by silica gel column chromatography (hexane:ethyl acetate=5:1), the intended free type compound was obtained in brown oily substance. Next, an ethanol solution (172 mL) containing maleic acid (13.5 g, 115 mmol) was dropwise added into the ethanol solution (345mL) containing the free type compound under reflux condition. The reaction solution was stirred for one hour at room temperature. The obtained crystal was filtered, washed with ethanol, dried to get the intended substance (41.3 g, 72% Yield).

Light yellow crystal, mp.; 201–202° C., $^1$H-NMR (DMSO-$d_6$) δ: 1.15 (s, 3H), 1.47 (s, 3H), 2.87–3.05 (m, 3H), 3.23–3.26 (m, 1 H), 3.35 (br.s, 1 H), 3.97 (dd, J=4.7 and 9.0 Hz, 1H), 4.42 (d, J=9.0 Hz, 1H), 6.08 (s, 2H), 6.21 (br.s, 1H), 7.20–7.35 (m, 5H), 7.60 (s, 1H), 7.84 (s, 2H). MS (EI) m/z; 343 [M+1]$^+$, 105 (bp).

PREPARATION EXAMPLES

Preparation Example 1

| Tablet: | |
|---|---:|
| a compound according to the invention | 10 g |
| lactose | 260 g |
| microcrystalline cellulose | 600 g |
| corn starch | 350 g |
| hydroxypropyl cellulose | 100 g |
| CMC-Ca | 150 g |
| magnesium stearate | 30 g |
| Total weight | 1,500 g |

The aforementioned ingredients were mixed by a conventional method and then 10,000 sugar-coated tablets each containing 1 mg of the active ingredient per tablet were prepared.

Preparation Example 2

| Capsule: | |
|---|---:|
| a compound according to the invention | 10 g |
| lactose | 440 g |
| microcrystalline cellulose | 1,000 g |
| magnesium stearate | 50 g |
| Total weight | 1,500 g |

The aforementioned ingredients were mixed by a conventional method and then filled into gelatin capsules to prepare 10,000 capsules each containing 1 mg of the active ingredient per capsule.

Preparation Example 3

| Soft capsule: | |
|---|---:|
| a compound according to the invention | 10 g |
| PEG 400 | 479 g |
| saturated fatty acid triglyceride | 1,500 g |
| peppermint oil | 1 g |
| Polysorbate 80 | 10 g |
| Total weight | 2,000 g |

The aforementioned ingredients were mixed by a conventional method and then filled into No. 3 soft gelatin capsules to prepare 10,000 soft capsules each containing 1 mg of the active ingredient per capsule.

Preparation Example 4

| Ointment: | |
|---|---:|
| a compound according to the invention | 1.0 g |
| liquid paraffin | 10.0 g |
| cetanol | 20.0 g |
| white vaseline | 68.4 g |
| ethylparaben | 0.1 g |
| l-menthol | 0.5 g |
| Total weight | 100.0 g |

The aforementioned ingredients were mixed by a conventional method to obtain 1% ointment.

Preparation Example 5

| Suppository: | |
|---|---:|
| a compound according to the invention | 1 g |
| Witepsol H15* | 478 g |
| Witepsol W35* | 520 g |
| Polysorbate 80 | 1 g |
| Total weight | 1,000 g |

(*trade name for triglyceride type compounds)

The aforementioned ingredients were melt-mixed by a conventional method, poured into suppository containers and cooled to solidify, and 1,000 suppositories (1 g) each containing 1 mg of the active ingredient per suppository were prepared.

Preparation Example 6

| Injection: | |
|---|---|
| a compound according to the invention | 1 mg |
| distilled water for injection | 5 mL |

It is used by dissolving when applied.

Pharmacological Test Example

Effects on the Effective Refractory Period

Method

Beagles were anesthetized with pentobarbital sodium and thoracotomy was done along the median line under a respirator and the incision was made on the pericardium to expose the heart. ECG was recorded using bipolar electrodes attached to the surface of the right atrial free wall, right atrial auricle, and right ventricular free wall. The vagal nerves were stimulated using an electrostimulation device with Nichrome wires inserted into the vagal nerves in the neck bilaterally. The conditions for electrostimulation to the vagal nerves were set such that the RR intervals on ECG were prolonged by about 100 msec compared with those before the stimulation was started.

Atrial and ventricular effective refractory periods were determined by S1-S2 extrastimulus technique at basic cycle length of 300 msec during bilateral vagal nerve stimulation, using programmable electric stimulator. A train of 10 basic stimuli (S1) was followed by a premature extrastimulus (S2) at 2 times diastolic threshold. The S1-S2 interval was successively decreased by 2 msec, and the effective refractory period was defined as the point at which S2 failed to produced a propagated response.

For evaluation of drug effects, the atrial and ventricular effective refractory periods were determined before drug administration, then respective compound was administrated intravenously at the dose of 0.3 mg/kg, and the atrial and ventricular effective refractory periods were determined from 5 min after the administration.

The results were shown as the prolongation time on the atrial and ventricular effective refractory periods, i.e. [effective refractory period after drug administration]−[effective refractory period before drug administration] (msec).

TABLE 6

| compound (Synthesis Example No.) | prolongation time on the effective refractory period (msec) | |
|---|---|---|
| | Atrium | Ventricle |
| 2 | 23 | 4 |
| 3 | 21 | 4 |
| 4 | 23 | −10 |
| 5 | 19 | 3 |
| 6 | 36 | 9 |

RESULTS

The compounds of the present invention showed the prolongation effect on the effective refractory period selective for atrium.

Effects of the Invention

Compounds according to the present invention exhibit the prolongation effect on the effective refractory period selective for atrium, thus can be used as an anti-atrial fibrillation agents and an supraventricular antiarrhythmic agent, and are useful as pharmaceuticals. Further, since compounds according to the present invention have small influence on ventricle, they can contribute to safe treatments of aforementioned arrhythmic conditions.

The invention claimed is:

1. A benzopyran compound of formula (1) or formula (2), or a pharmaceutically acceptable salt thereof:

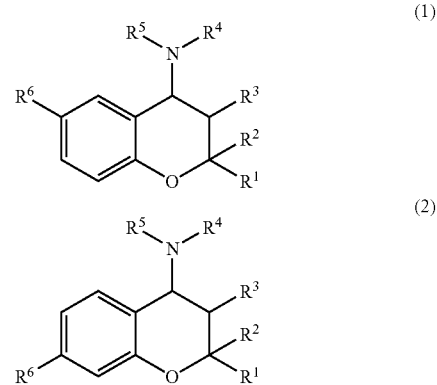

wherein $R^1$ and $R^2$ represent independently of each other hydrogen atom or $C_{1-6}$ alkyl group, wherein said alkyl group may be optionally substituted with halogen atom, $C_{1-6}$ alkoxy group or hydroxyl group;

$R^3$ represents hydroxyl group or $C_{1-6}$ alkylcarbonyloxy group;

$R^4$ hydrogen atom or $C_{1-6}$ alkyl group;

$R^5$ represents either (a) $C_{1-6}$ alkyl group substituted with $C_{6-14}$ aryl group or heteroaryl group, wherein said $C_{1-6}$ alkyl group may be optionally substituted with hydroxyl group or methyl group, and said $C_{6-14}$ aryl group or heteroaryl group may be optionally substituted with 1 to 3 $R^7$, wherein $R^7$ represents halogen atom, nitro group, cyano group, hydroyxl group, formyl group, formamide group, amino group, $C_{1-6}$ alkyl group optionally substituted with halogen atom, $C_{1-6}$ alkoxy group optionally substituted with halogen atom, $C_{3-6}$ cycloalkyl group, $C_{1-6}$ alkylamino group, di-$C_{1-6}$ alkylamino group, $C_{1-6}$ alkylcarbonylamino group, $C_{1-6}$ alkylsulfonylamino group, aminocarbonyl group, $C_{1-6}$ alkylaminocarbonyl group, di-$C_{1-6}$ alkylaminocarbonyl group, $C_{1-6}$ alkylcarbonyl group, $C_{1-6}$ alkoxycarbonyl group, aminosulfonyl group, $C_{1-6}$ alkylsulfonyl group, carboxyl group or benzoyl group wherein said benzoyl group may be optionally substituted with $C_{1-6}$ alkyl group, $C_{1-6}$ alkoxy group, halogen atom, nitro group or cyano group, or (b) straight-chain $C_{5-8}$ alkyl group, wherein said $C_{5-8}$ alkyl group may be optionally substituted with fluorine atom or hydroxyl group;

$R^6$ represents (a) $C_{1-6}$ alkyl group, wherein said alkyl group may be optionally substituted with hydroxyl group, carboxyl group, amino group, $C_{1-6}$ alkylamino group, di-$C_{1-6}$ alkylamino group, $C(O)OR^8$ $NHSO_2R^8$, $C(O)NH_2$, $C(O)NHR^8$, or $C(O)NR^8R^9$, wherein $R^8$ and $R^9$ represent independently of each other $C_{1-6}$ alkyl group substituted with $C_{6-14}$ aryl group or heteroaryl group or $C_{1-6}$ alkyl group, (b) $C_{1-6}$ alkoxy group, (c) halogen atom, (d) nitro group, (e) $C(O)NH_2$, (f) $C(O)NHR^8$ or (g) $C(O)NR^8R^9$ wherein $R^8$ and $R^9$ represent independently of each other $C_{1-6}$ alkyl group substituted with $C_{6-14}$ aryl group or heteroaryl group or $C_{1-6}$ alkyl group;

with a proviso that 4-benzylamino-3,4-dihydro-3-hydroxy-2,2-dimethyl-N-(2-phenylethyl)-2H-1-benzopyran-6-carboxamide and 4-(3-bromo-4-fluorobenzyl)amino-6-ethyl-3,4-dihydro2,2-dimethyl-2H-1-benzopyran-3-ol are excluded.

2. The benzopyran compound or pharmaceutically acceptable salt thereof according to claim 1, wherein both $R^1$ and $R^2$ represent methyl group, $R^3$ represents hydroxyl group and $R^4$ represents hydrogen atom.

3. The benzopyran compound or pharmaceutically acceptable salt thereof according to claim 2, wherein $R^5$ represents $C_{1-6}$ alkyl group substituted with $C_{6-14}$ aryl group.

4. The benzopyran compound or pharmaceutically acceptable salt thereof according to claim 3, wherein $R^6$ represents nitro group.

5. The benzopyran compound of the formula (2) or pharmaceutically acceptable salt thereof according to claim 4.

6. The benzopyran compound or pharmaceutically acceptable salt thereof according to claim 3, wherein $R^6$ represents $C(O)NH_2$.

7. The benzopyran compound or pharmaceutically acceptable salt thereof according to claim 3, wherein $R^6$ represents methyl group.

8. A pharmaceutical composition comprising a benzopyran compound or pharmaceutically acceptable salt thereof according to claim 1 as an active ingredient, which is administrated in a dosage of 0.003–1.5 g per day for an adult.

9. A pharmaceutical composition for treating arrhythmia comprising a benzopyran compound or pharmaceutically acceptable salt thereof according to claim 1 as an active ingredient, which is administered in a dosage of 0.003–1.5 g per day for an adult.

10. A pharmaceutical composition comprising a benzopyran compound or pharmaceutically acceptable salt thereof according to claim 1 as an active ingredient, wherein said composition contains said compound or salt thereof in an amount of about 0.01–99.5% based on the total weight of the composition.

11. The composition according to claim 10, wherein said composition is for treating arrhythmia.

* * * * *